United States Patent
Kato et al.

(10) Patent No.: US 6,359,184 B1
(45) Date of Patent: Mar. 19, 2002

(54) PROCESS FOR PRODUCTION OF XYLENE

(75) Inventors: Hajime Kato; Hitoshi Tanaka; Kazuyoshi Iwayama; Ryoji Ichioka, all of Nagoya (JP)

(73) Assignee: Toray Industries, Inc. (JP)

(*) Notice: Subject to any disclaimer, the term of this patent is extended or adjusted under 35 U.S.C. 154(b) by 0 days.

(21) Appl. No.: 09/487,538

(22) Filed: Jan. 19, 2000

Related U.S. Application Data

(62) Division of application No. 08/880,902, filed on Jun. 23, 1997, now Pat. No. 6,060,417.

(30) Foreign Application Priority Data

Jun. 28, 1996 (JP) .............................. 8-169665
Jul. 31, 1996 (JP) .............................. 8-202469

(51) Int. Cl.[7] .............................. C07C 6/00; C07C 4/18
(52) U.S. Cl. ...................... 585/321; 585/319; 585/470; 585/486; 585/488
(58) Field of Search .............................. 585/319, 321, 585/470, 486, 488

(56) References Cited

U.S. PATENT DOCUMENTS

| | | | |
|---|---|---|---|
| 3,306,944 A | * 2/1967 | Pollitzer | 585/485 |
| 3,476,821 A | 11/1969 | Brandenburg et al. | 585/475 |
| 3,527,825 A | * 9/1970 | Pollitzer | 585/474 |
| 4,177,219 A | * 12/1979 | Feinstein et al. | 585/489 |
| 4,181,811 A | * 1/1980 | Young | 585/486 |
| 4,320,242 A | * 3/1982 | Onodera et al. | 585/489 |
| 5,847,256 A | * 12/1998 | Ichioka et al. | 484/470 |
| 6,040,490 A | * 3/2000 | Ichioka et al. | 585/475 |

FOREIGN PATENT DOCUMENTS

| | | |
|---|---|---|
| EP | 0 731 071 A | 9/1996 |
| GB | 1 304 961 A | 1/1973 |
| GB | 1 395 114 A | 5/1975 |
| JP | 55 164631 A | 12/1980 |

* cited by examiner

*Primary Examiner*—Walter D. Griffin
(74) *Attorney, Agent, or Firm*—Schnader Harrison Segal & Lewis LLP

(57) ABSTRACT

Disclosed herein is a catalyst composition for transalkylation of alkylaromatic hydrocarbons which exhibits the percent conversion of ethyltoluene higher than 50 wt %, is composed of mordenite (100 pbw), inorganic oxide and/or clay (25–150 pbw), and at least one metal component of rhenium, platinum, and nickel, and contains mordenite such that the maximum diameter of secondary particles of mordenite is smaller than 10 μm. Disclosed also herein is a process for producing xylene by the aid of said catalyst from alkylaromatic hydrocarbons containing $C_9$ alkylaromatic hydrocarbons containing more than 5 wt % ethyltoluene and less than 0.5 wt % naphthalene, in the presence of hydrogen.

22 Claims, 2 Drawing Sheets

PROCESS FOR PRODUCTION OF XYLENE

CROSS-REFERENCE TO RELATED APPLICATION

This application is a division out of U.S. application Ser. No. 08/880,902, filed Jun. 23, 1997, now U.S. Pat. No. 6,060,417, granted on May 9, 2000.

BACKGROUND OF THE INVENTION

1. Field of the Invention

The present invention relates to a catalyst composition for transalkylation of alkylaromatic hydrocarbons and to a process for production of xylene. More particularly, the present invention relates to a catalyst composition for production of xylene from a feedstock containing $C_9$ alkylaromatic hydrocarbons by transalkylation and to a process for production of xylene.

2. Description of the Prior Art

Transalkylation of alkylaromatic hydrocarbons is one of the industrially important reactions which is applied to the production of benzene and xylene from toluene by disproportionation and the production of xylene from toluene and methylbenzene by transalkylation. There have been proposed a number of catalyst systems for this reaction. Among them is crystalline aluminosilicate zeolite (such as faujasite and mordenite) which is known as an effective catalyst. Mordenite is particularly active in transalkylation of alkylaromatic hydrocarbons.

Unfortunately, mordenite used alone is not satisfactory in activity and catalyst life; therefore, it is used in combination with a metal from Group VIB (such as chromium, molybdenum, and tungsten) or a metal from Group VIII (such as iron, cobalt, nickel, and platinum metal), as disclosed in U.S. Pat. No. 3,729,521. In addition, there is disclosed a catalyst which substantially consists only of mordenite and rhenium, in Japanese Patent Publication No. 45849/1987. These catalysts, however, are not wholly effective for transalkylation in production of xylene from $C_9$ alkylaromatic hydrocarbons (including ethyltoluene). Incidentally, J. Das et al. reported transalkylation of feedstocks containing $C_9$ alkylaromatic hydrocarbons by β-zeolite (Catalysis Letters, vol. 23 (1994), p. 161–168). In actuality, this process is not satisfactory in xylene yields. Practically, there exists no efficient way of producing xylene from $C_9$ alkylaromatic hydrocarbons containing ethyltoluene.

SUMMARY OF THE INVENTION

It is an object of the present invention to provide a catalyst composition for efficient production of xylene from a feedstock containing $C_9$ alkylaromatic hydrocarbons by dealkylation and transalkylation. It is another object of the present invention to provide a process for producing xylene.

$C_9$ alkylaromatic hydrocarbons are of low industrial value and are usually consumed as fuel. The present inventors paid attention to ethyltoluene and trimethylbenzene contained in $C_9$ alkylaromatic hydrocarbons, because ethyltoluene can be converted into toluene by dealkylation and two moles of toluene or toluene and trimethylbenzene can be converted into xylene (which is industrially useful) by transalkylation. There has been no way of efficient dealkylation of ethyltoluene into toluene, which leads to low yields of xylene. The catalyst composition of the present invention is capable of efficient dealkylation of ethyltoluene into toluene and efficient production of xylene by transalkylation.

DESCRIPTION OF THE PREFERRED EMBODIMENTS

Figure 1:
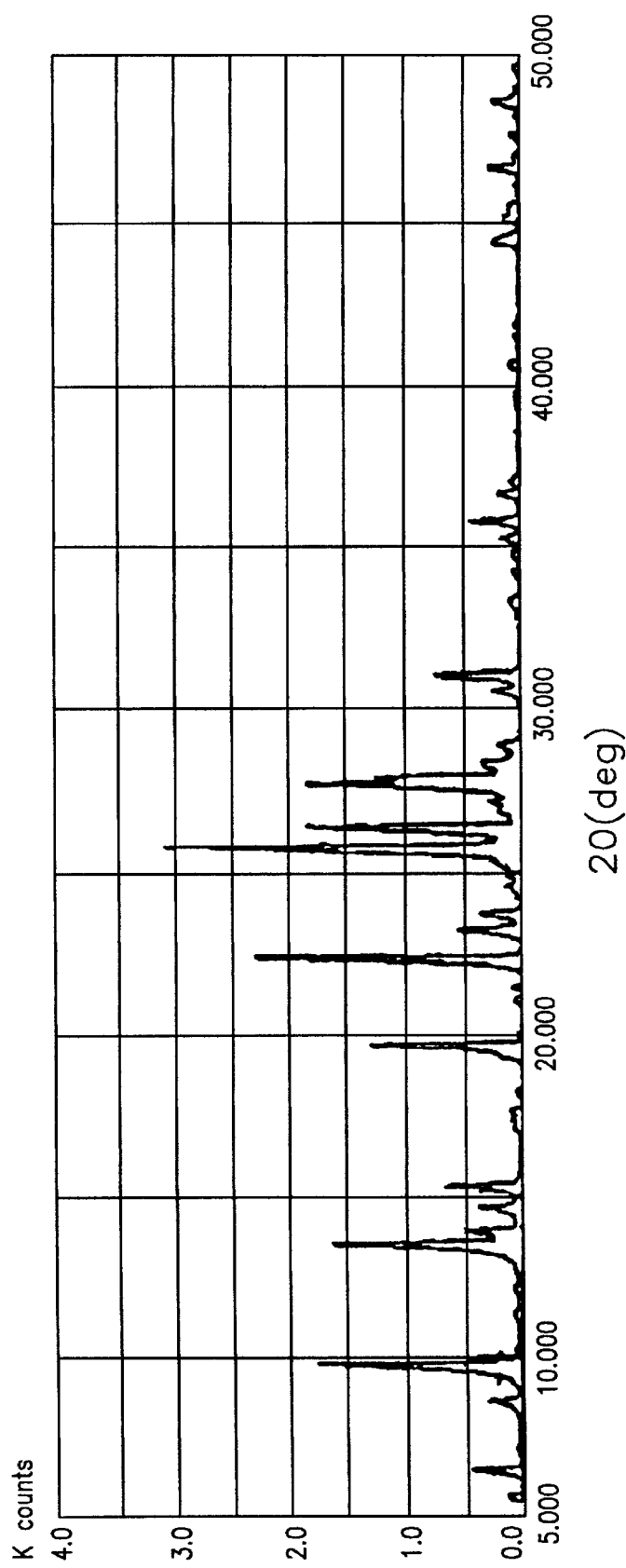
FIG. 1 is an X-ray diffraction pattern of the mordenite-type zeolite prepared in Example of the present invention.

The present invention is based on the present inventors' finding that the catalyst capable of efficient conversion of ethyltoluene as shown below is useful for production of xylene from ethyltoluene contained in $C_9$ alkylaromatic hydrocarbons through conversion into toluene by dealkylation and subsequent transalkylation of toluene or toluene and trimethylbenzene.

Conversion of ethyltoluene:

Feedstock:

Ratio of ethyltoluene to (trimethylbenzene plus ethyltoluene)=35 wt %

Reaction conditions:

| | |
|---|---|
| Temperature: | 400° C. |
| Pressure: | 3 MPa-G |
| WHSV (weight space velocity) | 2.5 $h^{-1}$ |
| Ratio of $H_2$ to feedstock: | 4.0 mol/mol |

Percent conversion of ethyltoluene (wt %)=(A–B)/A×100 where

A: concentration of ethyltoluene in feedstock (wt %)

B: concentration of ethyltoluene after reaction (wt %)

The catalyst which achieves the percent conversion of ethyltoluene higher than 50 wt %, preferably higher than 80 wt %, in the above-mentioned reaction is useful in the present invention.

In addition, the high percent conversion of ethyltoluene and the high yields of xylene by transalkylation are achieved by the catalyst composed of hydrogen-type mordenite, inorganic oxide and/or clay, and at least one metal (selected from rhenium, platinum, and nickel) in an adequate ratio. A detailed description follows. Ethyltoluene converts into toluene and ethylene upon dealkylation by hydrogen-type mordenite. The percent conversion of ethyltoluene is not sufficiently high due to restrictions by the thermodynamic equilibrium. These restrictions are eliminated if the catalyst is incorporated with an inorganic oxide and/or clay which densely supports at least one metal component (selected from rhenium, platinum, and nickel). This catalyst causes hydrogen present in the reaction system to hydrogenize ethylene (formed by dealkylation of ethyltoluene) into ethane. The result is a high percent conversion. The improved yield of xylene is due to transalkylation of toluene or toluene and trimethylbenzene. The metal component supported by the inorganic oxide and/or clay is responsible for hydrogenolysis of high boiling by-products. This suppresses the catalyst coking and deactivation and prolongs the catalyst life. These effects are produced only when requirements for an adequate composition are satisfied as mentioned above.

The zeolite used in the present invention is hydrogen-type mordenite. A preferred mordenite is one in which the silica/alumina molar ratio is from 15 to 30. This mordenite may be obtained from mordenite having a low silica/alumina molar ratio by acid extraction to eliminate aluminum or by direct synthesis. Directly synthesized mordenite is preferable. Synthesis of mordenite is disclosed in American Mineralogist, vol. 57 (1972), p. 1146–1151, and Japanese Patent Publication Nos. 51969/1985 and 31006/1990.

Conversion into hydrogen-type mordenite may be accomplished by direct ion exchange of mordenite (containing metal cations) with an acid or by ion exchange in an aqueous solution containing ammonium ions, for conversion into ammonium type, followed by drying and calcination. Conversion from ammonium type into hydrogen type is preferable. The ion exchange may be carried out before or after the forming of zeolite, with the latter method being industrially desirable. For improvement of catalytic performance, mordenite may optionally be treated with an organic acid containing carboxyl groups (such as lactic acid, malic acid, tartaric acid, and citric acid). The inorganic oxide and/or clay is essential as a support for at least one metal component selected from rhenium, platinum, and nickel. The inorganic oxide includes alumina, silica-alumina, silica, titania, and magnesia, with alumina being preferable. Alumina includes boehmite, boehmite gel, gibbsite, bialite, nordstrandite, diaspore, and amorphous alumina gel, with boehmite being preferable. Alumina of $\gamma$-, $\eta$-, and $\delta$-modifications (that occur under different calcination conditions) may be used. Alumina sol or alumina gel used as a binder to form the catalyst also functions as a support for the metal component (selected from rhenium, platinum, and nickel). The clay is natural or purified one, such as montmorillonite, kaolin, sepiolite, and acid clay, which are not specifically restricted. The amount of the inorganic oxide and/or clay in the catalyst should be 20–150 pbw, preferably 40–150 pbw, for 100 pbw of mordenite. Larger amounts than specified (with decreased amounts of mordenite) leads to low dealkylation and transalkylation activities. Smaller amounts than specified leads to short catalyst life and low ethyltoluene conversion and low xylene yields due to poor dispersion of metal components and hence poor hydrogenation of ethylene resulting from dealkylation of ethyltoluene.

It is essential in the present invention that the catalyst contain as the metal component at least one member selected from rhenium, platinum, and nickel. Rhenium may be present in any form, such as oxide, sulfide, and selenide. The amount of rhenium should be 0.05–1.5 pbw (as metal) for 100 pbw of mordenite and 0.1–2.0 pbw (as metal) for 100 pbw of inorganic oxide and/or clay. The catalyst with an excessively small amount of rhenium is poor in conversion of ethyltoluene. Conversely, the catalyst with an excessively large amount of rhenium causes excessive hydrogenolysis of alkylaromatic hydrocarbons. Preferred rhenium compounds include perrhenic acid and ammonium perrhenate. Preferred platinum compounds include chloroplatinic acid and ammonium chloroplatinate. The amount of platinum should be 0–0.005 pbw (as metal) for 100 pbw of mordenite. Preferred nickel compounds include water-soluble salts such as nitrate and acetate. The amount of nickel should be 0.05–1.5 pbw (as metal) for 100 pbw of mordenite. For these metal components to be supported, the mordenite is uniformly mixed with the inorganic oxide and/or clay, followed by forming, drying, and calcination, and the mordenite is converted into hydrogen type or ammonium type and finally impregnated with an aqueous solution containing at least one metal component of rhenium, platinum, and nickel. The resulting product is dried and calcined. Calcination changes the mordenite of ammonium type into the mordenite of hydrogen type. Calcination should preferably be carried out in an oxygen-containing atmosphere at 300–650° C.

The present inventors' investigation on the dealkylation of ethyltoluene into toluene, which is intended to produce xylene from ethyltoluene contained in $C_9$ alkylaromatic hydrocarbons by dealkylation and subsequent transalkylation of toluene or toluene and trimethyltoluene, revealed that secondary particles of mordenite in the formed catalyst play an important role. Secondary particles results from primary particles by aggregation. The diameter of secondary particles can be easily examined by means of a scanning electron microscope (SEM). For the object of the present invention, the maximum diameter of secondary particles of mordenite should be smaller than 10 $\mu$m, preferably smaller than 5 $\mu$m. Secondary particles will be partly broken and dispersed during the mixing and forming of the mordenite with the inorganic oxide and/or clay. Secondary particles of mordenite in the formed catalyst should be sufficiently small and well dispersed so that they readily interact with the metal component in the catalyst for a high percent conversion of ethyltoluene. The diameter of secondary particles of mordenite in the formed catalyst depends on the conditions under which the catalyst is formed and the diameter of secondary particles in raw material mordenite. It also varies depending on the kneading time and water content, and it becomes smaller according as the kneading time increases. The diameter of secondary particles in raw material mordenite powder depends on the mixing ratio of reactants, the time for crystallization, and the method of stirring and drying. It tends to become smaller according as the reaction mixture decreases in alkalinity and the time for crystallization also decreases.

The present invention is based on the present inventors' finding that it is possible to produce xylene efficiently from a feedstock containing $C_9$ alkylaromatic hydrocarbons such as ethyltoluene, trimethylbenzene, and propylbenzene, which are of low industrial value and mainly consumed as fuel, through dealkylation of ethyltoluene into toluene and transalkylation of toluene or toluene and trimethylbenzene into xylene. The percent conversion of ethyltoluene is higher than 50 wt %, preferably higher than 80 wt %. For high xylene yields, it is important that the $C_9$ alkylaromatic hydrocarbons contain ethyltoluene in an amount more than 5 wt %, preferably more than 10 wt %. The $C_9$ alkylaromatic hydrocarbons may contain $C_{10}$ compounds such as diethylbenzene, ethylxylene, tetramethylbenzene, and the like. Using a mixture of toluene and $C_9$ alkylaromatic hydrocarbons as a feedstock is embraced in the embodiments of the present invention. In this case, the mixing ratio of toluene and $C_9$ alkylaromatic hydrocarbons should preferably be in the range of 0:1 to 1:1 (by weight). The feedstock may contain, in addition to the above-mentioned aromatic hydrocarbons, non-aromatic hydrocarbons such as paraffin and naphthene. The catalyst pertaining to the present invention is used for the production of xylene mentioned above. It is essential that hydrogen be present in the reaction system for the production of xylene. The amount of hydrogen to be supplied should be such that the molar ratio of hydrogen to alkylaromatic hydrocarbons is in the range of 1 to 10. The reaction should be carried out at a pressure of 1–6 MPa, at a temperature of 300–550° C., and at a WHSV (weight space velocity) of 0.5–10 $h^{-1}$.

The present inventors' investigation revealed that trace constituents such as naphthalene present in the feedstock ($C_9$ alkylaromatic hydrocarbons) lowers the catalytic activity and reduces the xylene yields. The content of naphthalene in $C_9$ alkylaromatic hydrocarbons is typically about 1 wt %, although it varies depending on the sources. Therefore, it is important that alkylaromatic hydrocarbons (as feedstock), be distilled under normal pressure or reduced pressure prior to transalkylation to reduce the content of naphthalene below 0.5 wt %, preferably 0.3 wt %.

EXAMPLES

The invention will be described in more detail with reference to the following examples, which are not intended to restrict the scope of the invention.

Synthesis of mordenite-type zeolite

An aqueous solution was prepared by dissolving in 586.8 g of water 21.3 g of solid sodium hydroxide (containing 96.0 wt % NaOH and 4.0 wt % $H_2O$, from Katayama Kagaku) and 21.3 g of tartaric acid powder (containing 99.7 wt % tartaric acid and 0.3 wt % $H_2O$, from Katayama Kagaku). To this aqueous solution was added 29.2 g of sodium aluminate solution (containing 18.5 wt % $Al_2O_3$, 26.1 wt % NaOH, and 55.4 wt % $H_2O$, from Sumitomo Chemical). To the resulting uniform solution was slowly added with stirring 111.5 g of silicic acid powder (containing 91.6 wt % $SiO_2$, 0.33 wt % $Al_2O_3$, 0.27 wt % NaOH, "Nipseal VN-3" from Nippon Silica). There was obtained a uniform aqueous slurry having the following composition (in molar ratio).

| | | |
|---|---|---|
| $SiO_2/Al_2O_3$ | 30 | |
| $H_2O/SiO_2$ | 20 | |
| $OH^-/SiO_2$ | 0.25 | |
| $A/Al_2O_3$ | 2.5 | A: tartrate |

The slurry was heated at 160° C. for 72 hours with stirring (250 rpm) in a 1-liter autoclave. The reaction product was washed with distilled water and filtered five times and then dried overnight at about 120° C. Thus there was obtained a mordenite-type zeolite which has the composition of $1.02Na_2O \cdot Al_2O_3 \cdot 18.6SiO_2$ and gives an X-ray diffraction pattern shown in FIG. 1.

Forming

A paste mixture was prepared from 74.6 g of the mordenite powder prepared as mentioned above (containing 93.8 wt % mordenite), 39.5 g of alumina powder of boehmite structure (α-alumina monohydrate) (containing 76.1 wt % $Al_2O_3$, SCF type, from Condia), 80 g of alumina sol (containing 10 wt % $Al_2O_3$, "Colloidal Alumina 200", from Nissan Kagaku), 10 g of alumina gel powder (containing 70 wt % $Al_2O_3$, "Cataloid AP (C-10)", from Shokubai Kasei), and 10 g of distilled water. After kneading for about 1 hour, the paste was formed into pellets (1.2 mm in diameter and 1.0 mm long), which were dried overnight at 120° C. The dried pellets, equivalent to 90 g (dry basis), were calcined in air at 400° C. for 2 hours. On cooling in a desiccator, there was obtained the desired formed catalyst A.

Example 1

The formed catalyst A (15 g dry basis) was treated with 30 ml of 10 wt % aqueous solution of ammonium chloride at 80–85° C. for 1 hour. The treating solution was discarded and treatment was repeated with a fresh solution four times in the same manner as above. The treatment was followed by rinsing with distilled water five times. The formed catalyst A was further treated with 30 ml of 5 wt % aqueous solution of tartaric acid at 80–85° C. for 4 hours. The treating solution was discarded and the treatment was followed by rinsing with distilled water five times. For impregnation with rhenium, the formed catalyst A was immersed in 21 g of water containing 0.039 g of rhenium (VII) oxide ($Re_2O_7$) dissolved therein for 4 hours. After removal of the treating solution by filtration, the formed catalyst A was dried overnight at 120° C. and then calcined in air at 540° C. for 2 hours. Thus there was obtained the catalyst B, which contains 66.5 pbw of alumina and 0.152 pbw of rhenium (equivalent to 0.228 pbw for 100 pbw of alumina) for 100 pbw of mordenite (dry basis).

Example 2

The formed catalyst A (15 g dry-basis) was treated with 30 ml of 10 wt % aqueous solution of ammonium chloride at 80–85° C. for 1 hour. The treating solution was discarded and treatment was repeated with a fresh solution four times in the same manner as above. The treatment was followed by rinsing with distilled water five times. The formed catalyst A was further treated with 30 ml of 5 wt % aqueous solution of tartaric acid at 80–85° C. for 4 hours. The treating solution was discarded and the treatment was followed by rinsing with distilled water five times. For impregnation with platinum, the formed catalyst A was immersed in 21 g of water containing 0.0010 g of chloroplatinic acid ($H_2[PtCl_6] \cdot 6H_2O$) dissolved therein for 4 hours. After removal of the treating solution by filtration, the formed catalyst A was dried overnight at 120° C. and then calcined in air at 540° C. for 2 hours. Thus there was obtained the catalyst C, which contains 66.5 pbw of alumina and 0.004 pbw of platinum for 100 pbw of mordenite (dry basis).

Example 3

The same procedure as in Example 2 was repeated to give the catalyst D except that the chloroplatinic acid was replaced by 0.11 g of nickel nitrate ($Ni(NO_3)_2 \cdot 6H_2O$). The catalyst C contains 66.5 pbw of alumina and 0.247 pbw of nickel for 100 pbw of mordenite (dry basis).

Example 4

The catalysts B, C, and D were evaluated by conversion of a feedstock (composed of ethyltoluene and trimethylbenzene in a ratio specified below) into xylene under the following conditions in a fixed bed flow reactor. The results are shown in Table 1. Composition of feedstock:

Ratio of ethyltoluene to (ethyltoluene plus trimethylbenzene)=35 wt %

| | |
|---|---|
| Temperature | 400° C. |
| Pressure | 3 MPa-G |
| WHSV | 2.5 $h^{-1}$ |
| $H_2$/feedstock | 4.0 mol/mol |

TABLE 1

| Destination of catalyst | Metal content (pbw) per 100 pbw of mordenite | Conversion (wt %) of ethyltoluene | Xylene yields (g) per 100 g of feedstock |
|---|---|---|---|
| Catalyst B | Re 0.152 | 95.5 | 31.6 |
| Catalyst C | Pt 0.004 | 97.7 | 29.0 |
| Catalyst D | Ni 0.247 | 94.8 | 30.3 |

It is noted from Table 1 that the catalysts of the present invention exhibit the high activity of dealkylation and transalkylation and realizes the high yields of xylene.

Example 5

The same procedure as in Example 1 was repeated to give the catalyst E except that the amount of rhenium (VII) oxide was changed to 0.078 g. The catalyst E contains 66.5 pbw of alumina and 0.267 pbw of rhenium (equivalent to 0.401 pbw for 100 pbw of alumina) for 100 pbw of mordenite (dry basis).

Example 6

The same procedure as in Example 1 was repeated to give the catalyst F except that the amount of rhenium (VII) oxide was changed to 0.24 g. The catalyst F contains 66.6 pbw of alumina and 0.686 pbw of rhenium (equivalent to 1.03 pbw for 100 pbw of alumina) for 100 pbw of mordenite (dry basis).

Comparative Example 1

The same procedure as in Example 1 was repeated to give the catalyst G except that the treatment with rhenium (VII) oxide was omitted. The catalyst G contains 66.4 pbw of alumina for 100 pbw of mordenite (dry basis).

Comparative Example 2

The same procedure as in Example 1 was repeated to give the catalyst H except that the amount of rhenium (VII) oxide was changed to 0.0059 g. The catalyst H contains 66.5 pbw of alumina and 0.042 pbw of rhenium (equivalent to 0.063 pbw for 100 pbw of alumina) for 100 pbw of mordenite (dry basis).

Example 7

The same procedure as in Example 1 was repeated to give the catalyst I except that the amount of rhenium (VII) oxide was changed to 0.59 g. The catalyst I contains 66.5 pbw of alumina and 1.77 pbw of rhenium (equivalent to 2.66 pbw for 100 pbw of alumina) for 100 pbw of mordenite (dry basis).

Example 8

The catalysts B and E to I (varying in rhenium content) were evaluated in the same manner as in Example 4. The results are shown in Table 2. It is noted from Table 2 that the catalysts B, E, F, and I (containing 0.05 pbw of rhenium as metal) exhibit the high activity of dealkylation and transalkylation and realizes the high yield of xylene, whereas the catalyst I is slightly lower in xylene yields than the catalysts B, E, and F (due to decomposition of $C_9$ alkylaromatic hydrocarbons) despite its high percent conversion of ethyltoluene. It is understood that the preferred rhenium content is 0.05–1.5 pbw (as metal) for 100 pbw of mordenite. The catalysts G and H are poor in conversion of ethyltoluene and low in xylene yields.

TABLE 2

| Destination of catalyst | Rhenium content (pbw) per 100 pbw of mordenite | Conversion (wt. %) of ethyltoluene | Xylene yields (g) per 100 g of feedstock |
|---|---|---|---|
| Catalyst B | 0.152 | 95.5 | 31.6 |
| Catalyst E | 0.267 | 96.7 | 31.7 |
| Catalyst F | 0.686 | 98.1 | 30.7 |
| Catalyst G | 0 | 12.3 | 9.8 |
| Catalyst H | 0.042 | 48.7 | 19.0 |
| Catalyst I | 1.77 | 97.8 | 26.6 |

Comparative Example 3

A paste mixture was prepared from 106.6 g of the mordenite powder prepared as mentioned above (containing 93.8 wt % mordenite), 80 g of alumina sol (containing 10 wt % $Al_2O_3$, "Colloidal Alumina 200", from Nissan Kagaku), 10 g of alumina gel powder (containing 70 wt % $Al_2O_3$, "Cataloid AP (C-10)", from Shokubai Kasei), and 10 g of distilled water. After kneading for about 1 hour, the paste was formed into pellets (1.2 mm in diameter and 1.0 mm long), which were dried overnight at 120° C. The dried pellets, equivalent to 15 g dry base, were calcined in air at 400° C. for 2 hours. On cooling in a desiccator, there was obtained the desired formed catalyst.

The formed catalyst (15 g) was treated with 30 ml of 10 wt % aqueous solution of ammonium chloride at 80–85° C. for 1 hour. The treating solution was discarded and treatment was repeated with a fresh solution four times in the same manner as above. The treatment was followed by rinsing with distilled water five times. The formed catalyst was further treated with 30 ml of 5 wt % aqueous solution of tartaric acid at 80–85° C. for 4 hours. The treating solution was discarded and the treatment was followed by rinsing with distilled water five times. For impregnation with rhenium, the formed catalyst was immersed in 21 g of water containing 0.039 g of rhenium (VII) oxide ($Re_2O_7$) dissolved therein for 4 hours. After removal of the treating solution by filtration, the formed catalyst was dried overnight at 120° C. and then calcined in air at 540° C. for 2 hours. Thus there was obtained the catalyst J, which contains 15.5 pbw of alumina and 0.067 pbw of rhenium (equivalent to 0.433 pbw for 100 pbw of alumina) for 100 pbw of mordenite (dry basis).

Comparative Example 4

A paste mixture was prepared from 32.1 g of the mordenite powder prepared as mentioned above (containing 93.8 wt % mordenite), 92.0 g of alumina powder of boehmite structure (α-alumina monohydrate) (containing 76.1 wt % $Al_2O_3$, SCF type, from Condia Co.), 80 g of alumina sol (containing 10 wt % $Al_2O_3$, "Colloidal Alumina 200", from Nissan Kagaku), 10 g of alumina gel powder (containing 70 wt % $Al_2O_3$, "Cataloid AP (C-10)", from Shokubai Kasei), and 10 g of distilled water. After kneading for about 1 hour, the paste was formed into pellets (1.2 mm in diameter and 1.0 mm long), which were dried overnight at 120° C. The dried pellets, equivalent to 15 g dry basis, were calcined in air at 400° C. for 2 hours. On cooling in a desiccator, there was obtained the desired formed catalyst.

The formed catalyst (15 g) was treated with 30 ml of 10 wt % aqueous solution of ammonium chloride at 80–85° C. for 1 hour. The treating solution was discarded and treatment was repeated with a fresh solution four times in the same manner as above. The treatment was followed by rinsing with distilled water five times. The formed catalyst was further treated with 30 ml of 5 wt % aqueous solution of tartaric acid at 80–85° C. for 4 hours. The treating solution was discarded and the treatment was followed by rinsing with distilled water five times. For impregnation with rhenium, the formed catalyst was immersed in 21 g of water containing 0.039 g of rhenium (VII) oxide ($Re_2O_7$) dissolved therein for 4 hours. After removal of the treating solution by filtration, the formed catalyst was dried overnight at 120° C. and then calcined in air at 540° C. for 2 hours. Thus there was obtained the catalyst K, which contains 293.3 pbw of alumina and 0.591 pbw of rhenium (equivalent to 0.201 pbw for 100 pbw of alumina) for 100 pbw of mordenite (dry basis).

Example 9

The catalysts B, J, and K (varying in mordenite content and alumina content) were evaluated in the same manner as in Example 4. The results are shown in Table 3. It is noted from Table 3 that the catalyst B (containing 20–150 pbw of alumina for 100 pbw of mordenite) exhibits the high activity of dealkylation and transalkylation and realizes the high xylene yields.

TABLE 3

| Destination of catalyst | Alumina content (pbw) per 100 pbw of mordenite | Conversion (wt %) of ethyltoluene | Xylene yields (g) per 100 g of feedstock |
|---|---|---|---|
| Catalyst B | 66.5 | 95.5 | 31.6 |
| Catalyst J | 15.5 | 47.7 | 18.4 |
| Catalyst K | 293.3 | 45.9 | 17.6 |

Example 10

The catalysts B, H, and J were evaluated in the same manner as in Example 4 to see how the xylene yields change with time. The results are shown in Table 4. It is noted from Table 4 that the catalyst B (containing 20–150 pbw of alumina and at least 0.05 pbw (as metal) of rhenium for 100 pbw of mordenite) exhibits the high activity which lasts for a long period of time.

TABLE 4

| | Xylene yields (g) per 100 g of feedstock | |
|---|---|---|
| Catalyst designation | After 6 hours | After 500 hours |
| Catalyst B | 31.6 | 31.2 |
| Catalyst H | 19.0 | 11.8 |
| Catalyst J | 18.4 | 9.9 |

Example 11

A paste mixture was prepared from 74.5 g of mordenite powder (JRC-Z-M 15, silica/alumina molar ratio=15.0, mordenite content 93.9 wt %) as the reference catalyst specified by the Society of Catalyst, the Committee of Reference Catalyst, 39.4 g of alumina powder of boehmite structure (α-alumina monohydrate) (containing 76.1 wt % $Al_2O_3$, SCF type, from Condia Co.), 80 g of alumina sol (containing 10 wt % $Al_2O_3$, "Colloidal Alumina 200", from Nissan Kagaku), 10 g of alumina gel powder (containing 70 wt % $Al_2O_3$, "Cataloid AP (C-10)", from Shokubai Kasei), and 10 g of distilled water. After kneading for about 1 hour, the paste was formed into pellets (1.2 mm in diameter and 1.0 mm long), which were dried overnight at 120° C. The dried pellets, equivalent to 15 g dry base, were calcined in air at 400° C. for 2 hours. On cooling in a desiccator, there was obtained the desired formed catalyst.

The formed catalyst (15 g) was treated with 30 ml of 10 wt % aqueous solution of ammonium chloride at 80–85° C. for 1 hour. The treating solution was discarded and treatment was repeated with a fresh solution four times in the same manner as above. The treatment was followed by rinsing with distilled water five times. For impregnation with rhenium, the formed catalyst was immersed in 21 g of water containing 0.039 g of rhenium (VII) oxide ($Re_2O_7$) dissolved therein for 4 hours. After removal of the treating solution by filtration, the formed catalyst was dried overnight at 120° C. and then calcined in air at 540° C. for 2 hours. Thus there was obtained the catalyst L, which contains 67.1 pbw of alumina and 0.157 pbw of rhenium (equivalent to 0.234 pbw for 100 pbw of alumina) for 100 pbw of mordenite (dry base).

Example 12

The same procedure as in Example 11 was repeated to give the catalyst M, except that the mordenite powder was replaced by 75.2 g of mordenite powder (JRC-Z-M 20, silica/alumina molar ratio=20.1, mordenite content 93.1 wt %) as the reference catalyst specified by the Society of Catalyst, the Committee of Reference Catalyst. The catalyst M contains 66.5 pbw of alumina and 0.168 pbw of rhenium (equivalent to 0.253 pbw for 100 pbw of alumina) for 100 pbw of mordenite (dry base).

Comparative Example 5

The same procedure as in Example 11 was repeated to give the catalyst N, except that the mordenite powder was replaced by 76.1 g of mordenite powder (JRC-Z-M 10, silica/alumina molar ratio=9.8, mordenite content 92.0 wt %) as the reference catalyst specified by the Society of Catalyst, the Committee of Reference Catalyst. The catalyst N contains 68.2 pbw of alumina and 0.157 pbw of rhenium (equivalent to 0.230 pbw for 100 pbw of alumina) for 100 pbw of mordenite (dry base).

Example 13

An amount of 107.4 g of mordenite powder (JRC-Z-M 20) was treated with 200 ml of conc. hydrochloric acid at 80–85° C. for 24 hours. The treating solution was discarded by filtration and the treated mordenite powder was washed repeatedly with distilled water until chlorine ions were not detected any longer in the washings and then dried overnight at 120° C. A paste mixture was prepared from 70 g of the treated mordenite powder (silica/alumina molar ratio=28.1), 39.4 g of alumina powder of boehmite structure (α-alumina monohydrate) (containing 76.1 wt % $Al_2O_3$, SCF type, from Condia Co.), 80 g of alumina sol (containing 10 wt % $Al_2O_3$, "Colloidal Alumina 200", from Nissan Kagaku), 10 g of alumina gel powder (containing 70 wt % $Al_2O_3$, "Cataloid AP (C-10)", from Shokubai Kasei), and 10 g of distilled water. After kneading for about 1 hour, the paste was formed into pellets (1.2 mm in diameter and 1.0 mm long), which were dried overnight at 120° C. The dried pellets, equivalent to 15 g dry base, were calcined in air at 400° C. for 2 hours. On cooling in a desiccator, there was obtained the desired formed catalyst.

For impregnation with rhenium, the formed catalyst was immersed in 21 g of water containing 0.039 g of rhenium (VII) oxide ($Re_2O_7$) dissolved therein for 4 hours. After removal of the treating solution by filtration, the formed catalyst was dried overnight at 120° C. and then calcined in air at 540° C. for 2 hours. Thus there was obtained the catalyst 0, which contains 65.9 pbw of alumina and 0.148 pbw of rhenium (equivalent to 0.224 pbw for 100 pbw of alumina) for 100 pbw of mordenite (dry base).

Comparative Example 6

An amount of 107.4 g of mordenite powder (JRC-Z-M 20) was treated with 200 ml of conc. hydrochloric acid at 80–85° C. for 24 hours. The treatment was repeated with 200 ml of fresh conc. hydrochloric acid in the same manner as above. The treating solution was discarded by filtration and the treated mordenite powder was washed repeatedly with distilled water until chlorine ions were not detected any longer in the washings and then dried overnight at 120° C. A paste mixture was prepared from 70 g of the treated mordenite powder (silica/alumina molar ratio=35.3), 39.4 g of alumina powder of boehmite structure (α-alumina monohydrate) (containing 76.1 wt % $Al_2O_3$, SCF type, from Condia Co.), 80 g of alumina sol (containing 10 wt % $Al_2O_3$, "Colloidal Alumina 200", from Nissan Kagaku), 10 g of alumina gel powder (containing 70 wt % $Al_2O_3$, "Cataloid AP (C-10)", from Shokubai Kasei), and 10 g of distilled water. After kneading for about 1 hour, the paste was formed into pellets (1.2 mm in diameter and 1.0 mm long), which were dried overnight at 120° C. The dried pellets, equivalent to 15 g dry base, were calcined in air at 400° C. for 2 hours. On cooling in a desiccator, there was obtained the desired formed catalyst.

For impregnation with rhenium, the formed catalyst was immersed in 21 g of water containing 0.039 g of rhenium (VII) oxide ($Re_2O_7$) dissolved therein for 4 hours. After removal of the treating solution by filtration, the formed catalyst was dried overnight at 120° C. and then calcined in air at 540° C. for 2 hours. Thus there was obtained the catalyst P, which contains 65.9 pbw of alumina and 0.163 pbw of rhenium (equivalent to 0.247 pbw for 100 pbw of alumina) for 100 pbw of mordenite (dry base).

Examples 14

The catalysts L to P (varying in the silica/alumina molar ratio of mordenite) were evaluated in the same manner as in Example 4. The results are shown in Table 5. It is noted from Table 5 that the catalysts L, M, and O (containing mordenite whose silica/alumina molar ratio is from 15 to 30) exhibits the high activity of dealkylation and transalkylation and realizes the high xylene yields.

TABLE 5

| Destination of catalyst | Silica/alumina molar ratio | Conversion (wt %) of ethyltoluene | Xylene yields (g) per 100 g of feedstock |
| --- | --- | --- | --- |
| Catalyst L | 15.0 | 93.2 | 31.0 |
| Catalyst M | 20.1 | 94.7 | 31.5 |
| Catalyst N | 9.8 | 46.2 | 18.0 |
| Catalyst O | 28.1 | 91.5 | 30.6 |
| Catalyst P | 35.3 | 48.8 | 18.8 |

Example 15

A paste mixture was prepared from 74.6 g of the mordenite powder prepared as mentioned above (containing 93.8 wt % mordenite), 39.5 g of alumina powder of boehmite structure (α-alumina monohydrate) (containing 76.1 wt % $Al_2O_3$, SCF type, from Condia Co.), 80 g of alumina sol (containing 10 wt % $Al_2O_3$, "Colloidal Alumina 200", from Nissan Kagaku), 10 g of alumina gel powder (containing 70 wt % $Al_2O_3$, "Cataloid AP (C-10)", from Shokubai Kasei), and 10 g of distilled water. After kneading for about 5 hours, the paste was formed into pellets (1.2 mm in diameter and 1.0 mm long), which were dried overnight at 120° C. The dried pellets, equivalent to 90 g dry base, were calcined in air at 400° C. for 2 hours. On cooling in a desiccator, there was obtained the desired formed catalyst Q.

The formed catalyst Q (15 g) was treated with 30 ml of 10 wt % aqueous solution of ammonium chloride at 80–85° C. for 1 hour. The treating solution was discarded and treatment was repeated with a fresh solution four times in the same manner as above. The treatment was followed by rinsing with distilled water five times. The formed catalyst Q was further treated with 30 ml of 5 wt % aqueous solution of tartaric acid at 80–85° C. for 4 hours. The treating solution was discarded and the treatment was followed by rinsing with distilled water five times. For impregnation with rhenium, the formed catalyst Q was immersed in 21 g of water containing 0.039 g of rhenium (VII) oxide ($Re_2O_7$) dissolved therein for 4 hours. After removal of the treating solution by filtration, the formed catalyst Q was dried overnight at 120° C. and then calcined in air at 540° C. for 2 hours. Thus there was obtained the catalyst R, which contains 66.5 pbw of alumina and 0.159 pbw of rhenium (equivalent to 0.239 pbw for 100 pbw of alumina) for 100 pbw of mordenite (dry base).

Comparative Example 7

A paste mixture was prepared from 74.6 g of the mordenite powder prepared as mentioned above (containing 93.8 wt % mordenite), 39.5 g of alumina powder of boehmite structure (α-alumina monohydrate) (containing 76.1 wt % $Al_2O_3$, SCF type, from Condia Co.), 80 g of alumina sol (containing 10 wt % $Al_2O_3$, "Colloidal Alumina 200", from Nissan Kagaku), 10 g of alumina gel powder (containing 70 wt % $Al_2O_3$, "Cataloid AP (C-10)", from Shokubai Kasei), and 10 g of distilled water. After kneading for about 20 minutes, the paste was formed into pellets (1.2 mm in diameter and 1.0 mm long), which were dried overnight at 120° C. The dried pellets, equivalent to 90 g dry base, were calcined in air at 400° C. for 2 hours. On cooling in a desiccator, there was obtained the desired formed catalyst S.

The formed catalyst S (15 g) was treated with 30 ml of 10 wt % aqueous solution of ammonium chloride at 80–85° C. for 1 hour. The treating solution was discarded and treatment was repeated with a fresh solution four times in the same manner as above. The treatment was followed by rinsing with distilled water five times.. The formed catalyst S was further treated with 30 ml of 5 wt % aqueous solution of tartaric acid at 80–85° C. for 4 hours. The treating solution was discarded and the treatment was followed by rinsing with distilled water five times. For impregnation with rhenium, the formed catalyst S was immersed in 21 g of water containing 0.039 g of rhenium (VII) oxide ($Re_2O_7$) dissolved therein for 4 hours. After removal of the treating solution by filtration, the formed catalyst S was dried overnight at 120° C. and then calcined in air at 540° C. for 2 hours. Thus there was obtained the catalyst T, which contains 66.4 pbw of alumina and 0.161 pbw of rhenium (equivalent to 0.242 pbw for 100 pbw of alumina) for 100 pbw of mordenite (dry base).

Example 16

Figure 2B:
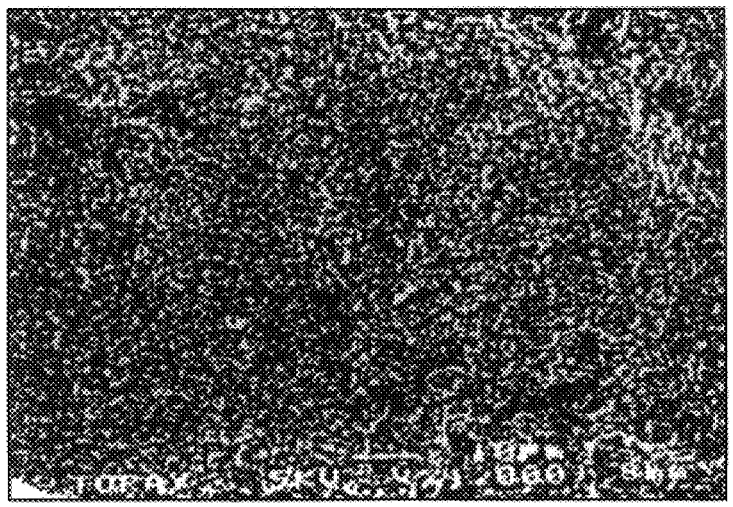
FIG. 2 is SEM photographs of catalysts B, R, and T prepared in Example of the present invention.
Figure 2R:
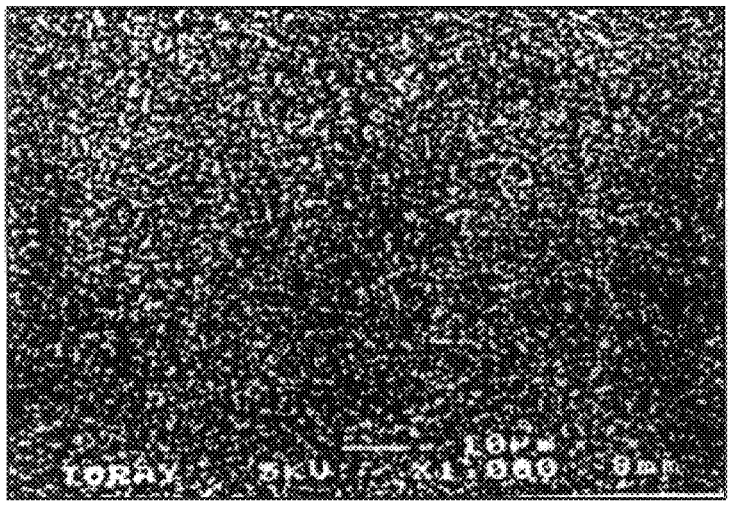
Figure 2T:
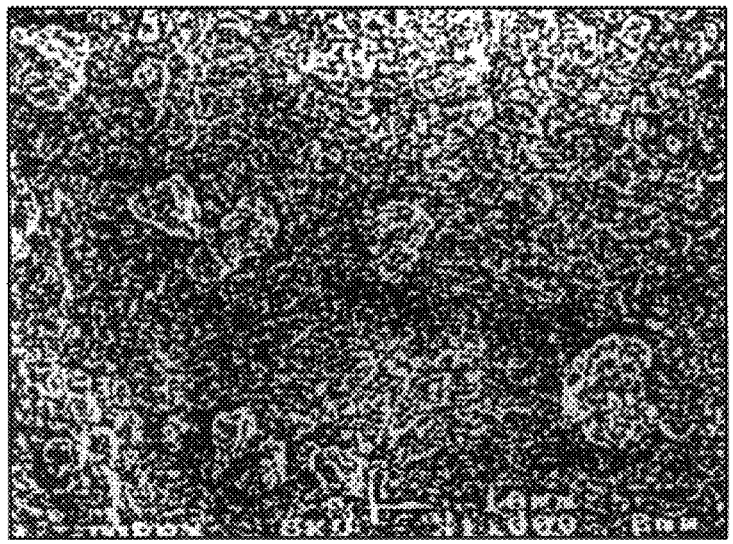

The catalysts B, R, and T (varying in the duration of kneading) were observed under an SEM to examine the maximum diameter of secondary particles of mordenite in the catalyst. The results are shown in Table 6, and SEM photographs are shown in FIG. 2. It is noted from Table 6 that the diameter of secondary particles of mordenite in the catalyst decreases according as the duration of kneading increases at the time of catalyst preparation.

TABLE 6

| Destination of catalyst | Maximum diameter of secondary particles of mordenite (μm) | Conversion (wt %) of ethyltoluene | Xylene yields (g) per 100 g of feedstock |
| --- | --- | --- | --- |
| Catalyst B | 7 | 95.5 | 31.6 |
| Catalyst R | 3 | 96.8 | 31.8 |
| Catalyst T | 20 | 78.9 | 25.1 |

Example 17

The catalysts B, Q, and R were evaluated in the same manner as in Example 4 to see how the catalytic performance is affected by the diameter of secondary particles of mordenite in the formed catalyst. The results are shown in Table 6. It is noted from Table 6 that the catalyst exhibits the higher activities of dealkylation and transalkylation according as the diameter of secondary particles of mordenite decreases. It is necessary that the maximum diameter of secondary particles be smaller than 10 μm.

Example 18

The catalyst B was evaluated in the same manner as in Example 1 using feedstocks varying in the ratio of trimethylbenzene (TMB for short) to ethyltoluene (ET for short). The results are shown in Table 7. It is noted from Table 7 that the xylene yields are high when the feedstocks contain more than 5 wt % ethyltoluene.

TABLE 7

| ET/(TMB + ET) ratio in feedstock (wt %) | Xylene yields (g) per 100 g of feedstock |
|---|---|
| 0 | 18.5 |
| 5 | 20.8 |
| 10 | 23.2 |
| 20 | 37.3 |
| 35 | 31.6 |
| 50 | 31.1 |
| 65 | 27.7 |

Example 19

The catalyst B was evaluated in the same manner as in Example 4 using feedstocks incorporated with naphthalene to see how the performance of transalkylation is affected by naphthalene in $C_9$ alkylaromatic hydrocarbons. The results are shown in Table 8. It is noted from Table 8 that the xylene yields decrease according as the amount of naphthalene in feedstock increases. It is necessary that the amount of naphthalene in feedstock be less than 0.5 wt %.

TABLE 8

| Amount of naphthalene in feedstock (wt %) | Xylene yields (g) per 100 g of feedstock |
|---|---|
| 0 | 31.6 |
| 0.10 | 31.5 |
| 0.28 | 31.2 |
| 0.45 | 30.4 |
| 0.98 | 27.3 |

What is claimed is:

1. A process for producing xylene from alkylaromatic hydrocarbons containing C9 alkylaromatic hydrocarbons, said process comprising dealkylation to convert ethyltoluene into toluene and subsequent transalkylation to convert toluene or toluene and trimethylbenzene in the C9 alkylaromatic hydrocarbons into xylene,
in the presence of a catalyst composition for transalkylation of alkylaromatic C9 hydrocarbons to toluene, comprising: (a) 100 pbw of a hydrogen-type mordenite;
(b) at least one material selected from the group consisting of an inorganic oxide and a clay and present in an amount of 40 to 150 parts by weight per 100 parts by weight of mordenite; and
(c) at least one metallic substance supported on said support material and comprising a metal or metallic compound selected from the group consisting of platinum and nickel compounds, wherein said metallic substance is provided in the following concentration ranges expressed as parts by weight ("pbw") of the metal component per 100 parts by weight of said mordenite:
platinum: not more than 0.005
nickel: 0.05–1.5.

2. A process for producing xylene as defined in claim 1, wherein the percent conversion of ethyltoluene is at least 50 wt %.

3. A process for producing xylene as defined in claim 1, wherein the percent conversion of ethyltoluene is at least 80 wt %.

4. A process for producing xylene as defined in claim 1, wherein the catalyst composition for transalkylation of alkylaromatic hydrocarbons is brought into contact with a feedstock of alkylaromatic hydrocarbons containing $C_9$ alkylaromatic hydrocarbons containing at least 5 wt % ethyltoluene in the presence of hydrogen.

5. A process for producing xylene as defined in claim 1 comprising reacting by transalkylation reaction from alkylaromatic hydrocarbons containing $C_9$ alkylaromatic hydrocarbons in the presence of hydrogen by the aid of a solid acid catalyst, characterized in that the alkylaromatic hydrocarbon contains less than 0.5 wt % naphthalene.

6. A process for producing xylene by transalkylation from alkylaromatic hydrocarbons as defined in claim 5, wherein the alkylaromatic hydrocarbon contains less than 0.3 wt % naphthalene.

7. A process for producing xylene as defined in claim 6, wherein the $C_9$ alkylaromatic hydrocarbons are subjected to distillation prior to transalkylation.

8. A process for producing xylene as defined in claim 5, wherein the solid acid catalyst is the catalyst for transalkylation of alkylaromatic hydrocarbons, wherein the amount of said inorganic oxide and/or clay is 25–150 pbw and the amount of said metal is at least 0.05 pbw, expressed as the metal, for 100 pbw of mordenite.

9. A process for producing xylene as defined in claim 1, wherein the alkylaromatic hydrocarbon as the feedstock contains less than 0.5 wt % naphthalene.

10. A process for producing xylene as defined in claim 9, wherein the alkylaromatic hydrocarbons contain less than 0.3 wt % naphthalene.

11. A process for producing xylene as defined in claim 9, wherein the C9 alkyl-aromatic hydrocarbon is subjected to distillation prior to transalkylation.

12. A process for producing xylene from alkylaromatic hydrocarbons containing C9 alkylaromatic hydrocarbons, said process comprising dealkylation to convert ethyltoluene into toluene and subsequent transalkylation to convert toluene or toluene and trimethylbenzene in the C9 alkylaromatic hydrocarbons into xylene,
in the presence of a catalyst composition for transalkylation of alkylaromatic C9 hydrocarbons to toluene, comprising:
(a) 100 pbw of a hydrogen-type mordenite;
(b) 40–150 pbw of at least one support member selected from the group consisting of an inorganic oxide and a clay; and
(c) a substance comprising rhenium, said substance being present in an amount ranging from about 0.1 to 2.0 parts by weight of said rhenium, expressed as weight of metal, per 100 parts by weight of said support member, said rhenium being present in an amount of at least 0.05 parts, expressed as metal per 100 parts of said mordenite,
wherein said catalyst has the ability to achieve the percent conversion of ethyltoluene of higher than 50 under the following conditions:

Ratio of ethyltoluene to (trimethylbenzene plus ethyltoluene)=35 wt %

Reactions conditions:

| | |
|---|---|
| Temperature: | 400° C. |
| Pressure: | 3 MPa-G |
| WHSV (weight space velocity): | 2.1 h$^{-1}$ |
| H2/feedstock: | 4.0 mol/mol |

Percent conversion of ethyltoluene (wt %)=(A−B)/A×100 where

A: concentration of ethyltoluene in feedstock (wt %)

B: concentration of ethyltoluene after reaction (wt %).

13. A process for producing xylene as defined in claim 12, wherein the percent conversion of ethyltoluene is at least 50 wt %.

14. A process for producing xylene as defined in claim 12, wherein the percent conversion of ethyltoluene is at least 80 wt %.

15. A process for producing xylene as defined in claim 12, wherein the catalyst composition for transalkylation of alkylaromatic hydrocarbons is brought into contact with a feedstock of alkylaromatic hydrocarbons containing C9 alkylaromatic hydrocarbons containing at least 5 wt % ethyltoluene in the presence of hydrogen.

16. A process for producing xylene as defined in claim 12 comprising reacting by transalkylation reaction from alkylaromatic hydrocarbons containing C9 alkylaromatic hydrocarbons in the presence of hydrogen by the aid of a solid acid catalyst, characterized in that the alkylaromatic hydrocarbon contains less than 0.5 wt % naphthalene.

17. A process for producing xylene by transalkylation from alkylaromatic hydrocarbons as defined in claim 16, wherein the alkylaromatic hydrocarbon contains less than 0.3 wt % naphthalene.

18. A process for producing xylene by transalkylation from alkylaromatic hydrocarbons as defined in claim 16, wherein the C9 alkylaromatic hydrocarbons are subjected to distillation prior to transalkylation.

19. A process for producing xylene as defined in claim 16, wherein the solid acid catalyst is the catalyst for transalkylation of alkylaromatic hydrocarbons, wherein the amount of said inorganic oxide and/or clay is 25–150 pbw and the amount of said metal is at least 0.05 pbw, expressed as the metal, for 100 pbw of mordenite.

20. A process for producing xylene as defined in claim 12, wherein the alkylaromatic hydrocarbon contains less than 0.5 wt % naphthalene.

21. A process for producing xylene as defined in claim 20, wherein the alkylaromatic hydrocarbons contain less than 0.3 wt % naphthalene.

22. A process for producing xylene as defined in claim 20, wherein the C9 alkyl-aromatic hydrocarbon is subjected to distillation prior to transalkylation.

* * * * *